US005905178A

United States Patent [19]
Hildreth

[11] Patent Number: 5,905,178
[45] Date of Patent: May 18, 1999

[54] REMOVAL OF α-METHYL STYRENE FROM CUMENE

[75] Inventor: James M. Hildreth, Wyckoff, N.J.

[73] Assignee: Catalytic Distillation Technologies, Pasadena, Tex.

[21] Appl. No.: 09/063,204

[22] Filed: Apr. 20, 1998

[51] Int. Cl.⁶ .............................. C07C 7/163; C07C 5/11
[52] U.S. Cl. .................... 585/258; 585/264; 585/269; 585/804; 203/DIG. 6
[58] Field of Search ..................... 585/258, 264, 585/269, 265, 270, 403, 804; 203/DIG. 6

[56] References Cited

U.S. PATENT DOCUMENTS

| | | | |
|---|---|---|---|
| 3,127,452 | 3/1964 | Codignola | 260/667 |
| 3,646,235 | 2/1972 | Little et al. | 260/667 |
| 4,158,611 | 6/1979 | Cooke | 203/28 |
| 4,334,107 | 6/1982 | Van Peppen | 568/749 |
| 4,410,755 | 10/1983 | Fisher et al. | 585/800 |
| 4,443,559 | 4/1984 | Smith, Jr. | 203/DIG. 6 |
| 4,822,936 | 4/1989 | Maurer et al. | 585/259 |
| 5,245,090 | 9/1993 | DeCaria et al. | 568/798 |

OTHER PUBLICATIONS

Hydrogenate AMS to Cumene, Hydrocarbon Processing, Int. Ed., vol. 59 #11, 1980 pp. 179–183.

Primary Examiner—Glenn Caldarola
Assistant Examiner—Thuan D. Dang
Attorney, Agent, or Firm—Kenneth H. Johnson

[57] ABSTRACT

A process for the removal of α-methyl styrene from admixtures with cumene by hydrogenation in a catalytic distillation hydrogenation to selectively hydrogenate the side chains and produce cumene is disclosed. The crude cumene may be the byproduct of the cumene oxidation to produce phenol. The crude cumene also contains acetone, benzene, ethyl benzene and high and low boiling carbonyls, which are either removed simultaneously with the hydrogenation/distillation or removed first followed by the selective catalytic distillation hydrogenation.

11 Claims, 2 Drawing Sheets

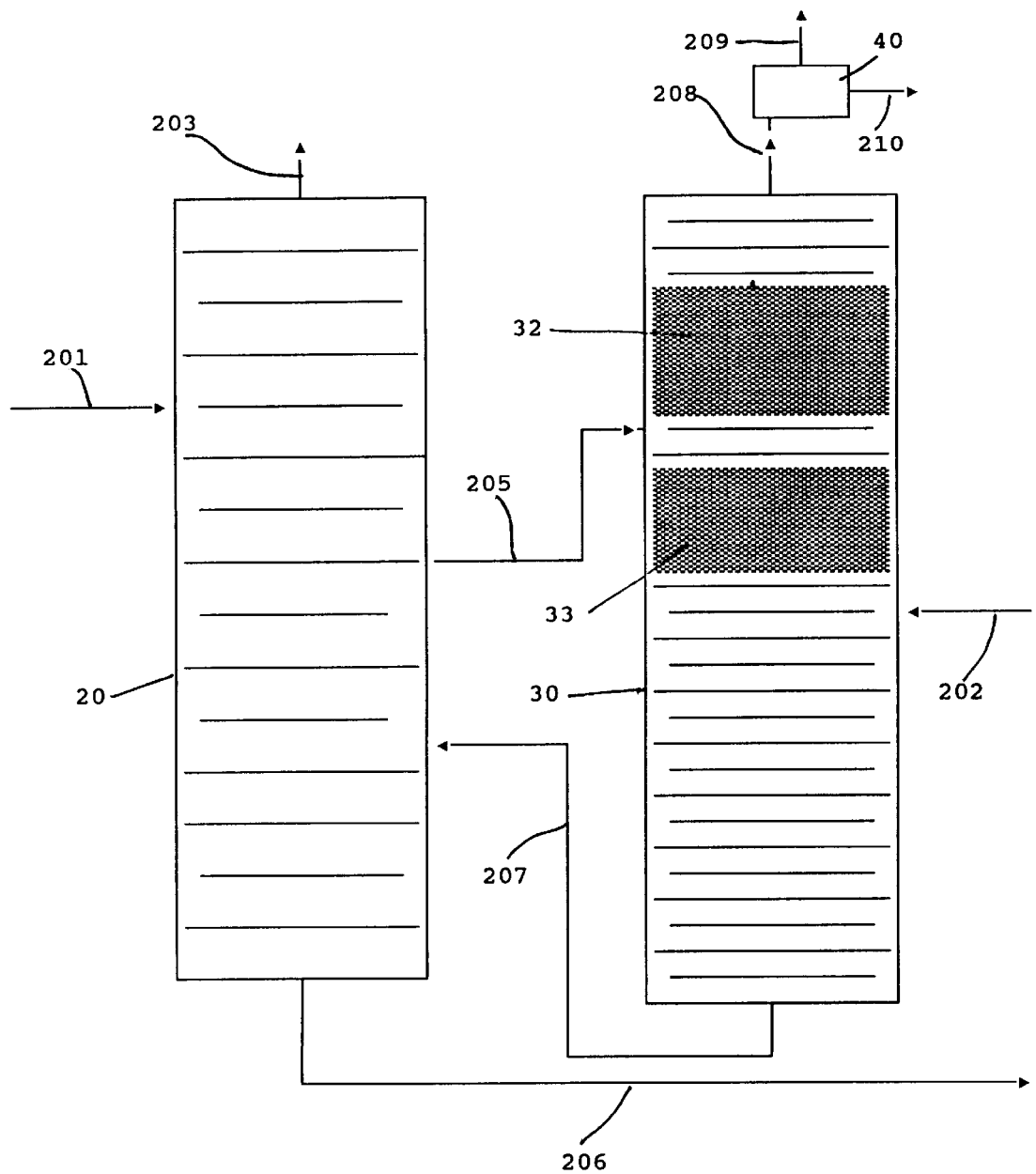

ered hydrocarbons is carried out simultaneously with the hydrogenation of the AMS. The cumene is then recycled to the oxidation reactor of the cumene/phenol process.

REMOVAL OF α-METHYL STYRENE FROM CUMENE

BACKGROUND OF THE INVENTION

1. Field of the Invention

The present invention relates to the purification of cumene. More particularly, the invention relates to the removal of the α-methyl styrene by selective hydrogenation of the side chain in a distillation column reactor. More particularly, the invention relates to a process wherein the α-methyl styrene is a byproduct from cumene hydroperoxidation phenol process.

2. Related Information

Substantial quantities of α-methyl styrene (AMS) are produced as a byproduct in the cumene-phenol peroxidation process. Purified cumene is oxidized to form cumene hydroperoxide (CHP) which is then cleaved to phenol and acetone. A small amount of AMS is produced as a byproduct from the decomposition of dimethylbenzyl alcohol which is also formed with CHP in the oxidation step. The AMS can either be recovered as a byproduct or hydrogenated to cumene and recycled to the phenol process. Since the market for AMS is limited, hydrogenation to cumene is the usual option. The typical composition of the cumene/AMS stream is 5 to 80% AMS with trace amounts of methyl benzofuran, mesityl oxide and acetophenone.

Previously, AMS hydrogenations employed a slurry type process using Raney nickel catalyst. The slurry process results in loss of aromatics and has been largely replaced by the fixed bed process. Although the process is effective, it requires two distillation towers and associated equipment, energy in the form of cooling and pressure.

In the first purification column, an AMS topping column, the cumene/AMS mixture which contains some light and heavier hydrocarbons including residual acetone, benzene, ethylbenzene and low and high boiling carbonyls is fractionated to recover the cumene/AMS as side draw which goes to a fixed bed straight pass hydrogenation reactor using palladium on alumina catalyst where AMS is hydrogenated to cumene in a concurrent flow.

Hydrogenation effluent containing mainly cumene with some unreacted AMS and heavies is fractionated in a second column where a bottoms purge is recycled to the topping column, and cumene is removed from the reflux to the oxidation system (phenol process).

U.S. Pat. No. 4,410,755 proposes a process of the purification of crude α-methyl styrene before hydrogenation by reacting it with acetol in an inert atmosphere in the presence of a noble metal of Group VIII of the periodic table to transfer hydrogen from the acetol to the α-methyl styrene and decomposing and sweeping away the resultant pyruvic aldehyde.

U.S. Pat. No. 4,822,936 discloses a selective hydrogenation process where a copper catalyst is supported on a gamma alumina. The process described therein is practiced at 0 (atmospheric pressure) to 10 psig and at temperatures of about 5 to 100° C. The preferred pressure is atmospheric (0 psig) and the preferred temperature is below 35° C. Palladium based hydrogenation catalysts have also been used but a large excess of hydrogen has been required resulting in hydrogenation of some of the styrene.

The use of a solid particulate catalyst as part of a distillation structure in a combination distillation column reactor for various reactions is described in U.S. Pat. Nos.: (etherification) 4,232,177; 4,307,254; 4,336,407; 4,504,687; 4,918,243; and 4,978,807; (dimerization) 4,242,530; (hydration) 4,982,022; (dissociation) 4,447,668; and (aromatic alkylation) 4,950,834 and 5,019,669. Additionally U.S. Pat. Nos. 4,302,356 and 4,443,559 disclose catalyst structures which are useful as distillation structures.

It is an advantage of the present invention that the active noble metals may be used to selectively hydrogenate the side chain of the α-methyl styrene. It is a further advantage that the present process will operate for longer periods without deactivation of the catalyst.

SUMMARY OF THE INVENTION

The present invention comprises the selective hydrogenation of α-methyl styrene in a distillation column reactor containing a hydrogenation catalyst which is preferably a component of a distillation structure in the presence of hydrogen at a mole ratio of greater than 1.0 relative to the α-methyl styrene concentration wherein the hydrogenation occurs simultaneously with the separation of the hydrogenation products preferably in a distillation column reactor. No more hydrogen than necessary to maintain the reaction is employed, since the excess hydrogen is usually vented.

The process for the selective hydrogenation of side chain in AMS in crude cumene/AMS comprises the steps of (a) feeding (1) a stream containing the crude cumene/AMS and (2) a stream containing hydrogen to a distillation column reactor having a distillation reaction zone containing a hydrogenation catalyst in the form of a catalytic distillation structure;

(b) concurrently in said distillation column reactor:
   (i) contacting the crude cumene/AMS containing stream with the hydrogen to selectively hydrogenate essentially all of the side chain of the AMS, and
   (ii) separating cumene by fractional distillation
   (iii) while operating said distillation column reactor at pressure of less than 50 psig, preferably in the range of subatmospheric to 45 psig and more preferably from atmospheric to 45 psig; and (c) withdrawing cumene, having substantially less AMS than the crude feed, from said distillation column reactor.

Because the reactor is operated as a distillation column reactor, better use of the hydrogen is achieved. Thus the reactor can preferably be operated at a low pressure, i.e., at less than 50 psig with the lower temperatures. Because a low pressure may be used, the more active noble metals such as palladium catalysts may be used and still maintain the desired selectivity due to the lower temperatures.

BRIEF DESCRIPTION OF THE DRAWING

FIG. 2 is a flow diagram in schematic form of a two column embodiment of the invention.

DESCRIPTION OF THE PREFERRED EMBODIMENT

Figure 1:
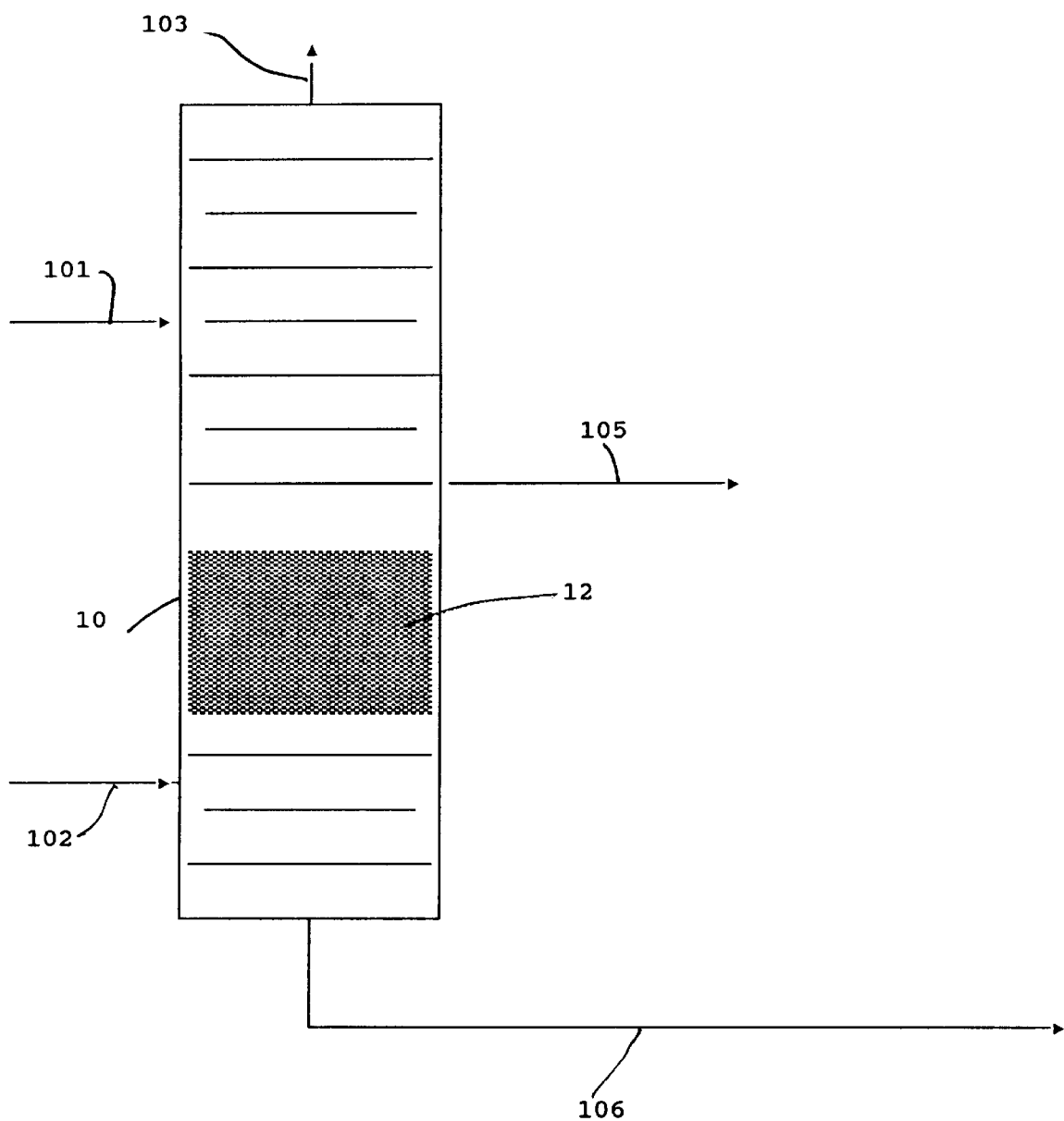
FIG. 1 is a flow diagram in schematic form of a one column embodiment of the invention.

The present invention is an improvement over the prior processes in that the hydrogenation catalyst structure may be placed in either of the two current distillation columns used to purify the unreacted cumene. Preferably the catalyst structure is placed in the first column which removes the lighter and heavier byproducts with a side draw to remove a cumene product stream for recycle. In so doing the fractionation and removal of the lighter and heavier residuals is achieved in the same manner as before. The catalytic distillation bed is positioned centrally in the column at a point just below the "cumene/AMS" side draw, and hydrogen fed from below while the crude mixture is fed into the column above the bed. This configuration allows the AMS/cumene mixture to move down into the bed and contact the hydrogen under the conditions described to hydrogenate the side chain such that the product from the side draw is high purity cumene rather than the cumene/AMS in the prior art configuration.

Hydrogenation carried out in a catalytic distillation column requires only a fraction of the hydrogen partial pressure required in the liquid phase processes which are the form of prior commercial operation for this type of stream, but gives the same or better result. Thus the capital investment and operating expense for the present hydrogenation are substantially lower than prior commercial operations. The lower hydrogen partial pressures allow for the use of the more active catalyst at the lower temperatures without unduly hydrogenating the vinyl aromatic.

Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the hydrogen and the AMS in the presence of the catalyst to result in the hydrogenation of the side chains.

The hydrogen rate must be adjusted such that it is sufficient to support the hydrogenation reaction and replace hydrogen lost from the catalyst. At least a stoichiometric amount of hydrogen relative to AMS must be present in the system to be available for the reaction. Also the nature of this reaction between a gas and a liquid and the apparent need to occlude the hydrogen into the liquid makes a small excess of hydrogen flow a preferred mode of operation.

In the usual application of a process where the catalyst serves as a distillation component, the equilibrium is constantly disturbed, thus driving the reaction toward completion, that is, the reaction has an increased driving force because the reaction products have been removed and cannot contribute to a reverse reaction (LeChatelier's Principle).

In the present process where there is no reversible reaction, no benefit is to be derived by removing the products of the reaction to increase the driving force of the reaction. Similarly the poor performance of prior vapor phase hydrogenations would not suggest the use of distillation type reaction. Thus, it is unexpected that catalytic distillation would be of benefit for non reversible hydrogenation.

It is believed that in the present catalytic distillation reaction is a benefit, first, because the reaction is occurring concurrently with distillation, the initial reaction products and other stream components are removed from the reaction zone as quickly as possible, reducing the likelihood of side reactions. Second, because all the components are boiling, the temperature of reaction is controlled by the boiling point of the mixture at the system pressure. The heat of reaction simply creates more boil up, but no increase in temperature at a given pressure. As a result, a great deal of control over the rate of reaction and distribution of products can be achieved by regulating the system pressure. Also, adjusting the throughput (residence time=liquid hourly space velocity$^{-1}$) gives further control of product distribution and to a degree control of the side reactions such as oligomerization. A further benefit that this reaction may gain from catalytic distillation is the washing effect that the internal reflux provides to the catalyst thereby reducing polymer build up and coking. Internal reflux may vary over the range of 0.2 to 20 L/D (wt. liquid just below the catalyst bed/wt. distillate).

The present invention carries out the method in a catalyst packed column which can be appreciated to contain a vapor phase and some liquid phase as in any distillation. The distillation column reactor is operated at a pressure such that the reaction mixture is boiling in the bed of catalyst. The present process operates at overhead pressure of said distillation column reactor preferably below 50 psig, so as to operate at temperatures within said distillation reaction zone in the range of 160 to 230° C. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.1 to 35.

The advantages of utilizing a distillation column reactor in the instant selective hydrogenation process lie in the better selectivity of the saturation of the side chain of the AMS without hydrogenation of the aromatic bonds, conservation of heat and the separation by distillation which can remove some other undesirable compounds, e.g. oxygenates, from the feed prior to further distillation and the distillation can concentrate desired components in the catalyst zone. Also, a separate hydrogenation reactor with its accompanying heat exchange equipment and controls is not necessary.

A "froth level" may be maintained throughout the catalyst bed by control of the bottoms and/or overheads withdrawal rate which improves the effectiveness of the catalyst thereby decreasing the height of catalyst needed. As may be appreciated the liquid is boiling and the physical state is actually a froth having a higher density than would be normal in a packed distillation column but less than the liquid without the boiling vapors, as described in U.S. Pat. No. 5,221,441 which is incorporated herein. Basically the froth mode called "liquid phase continuous (LPC)" hereafter is understood to mean that the flow of liquid from the catalytic distillation section has been restricted so that the rising vapor creates a froth. In effect the continuous phase is the liquid rather than the vapor as is usual in a distillation. The result is increased liquid contact with the catalytic material during the distillation and improved selective hydrogenation.

The temperature in the reactor is determined by the boiling point of the liquid mixture present at any given pressure. The temperature in the lower portions of the column will reflect the constitution of the material in that part of the column, which will be higher than the overhead. That is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa. As noted, the distillation column reactor is operated at low pressure to reduce the temperature to prevent unwanted polymerization and so that the better selectivity can be achieved.

As described, the catalytic material employed in the hydrogenation process is in a form to serve as distillation packing. Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel preferably deposited on a support such as alumina, fire brick, pumice, carbon, silica, resin or the like.

A preferred catalytic material comprises palladium oxide, preferably 0.1 to 5.0 weight %, supported on an appropriate support medium such as alumina, carbon or silica, e.g., ⅛" alumina extrudates. The gamma alumina supported copper based catalyst disclosed in U.S. Pat. No. 4,822,936 is also expected to be acceptable. In a preferred catalytic distillation structure the particulate catalyst material is disposed within a porous plate or screen to contain the catalyst and provide distillation surfaces in the form of a wire mesh structure, such as a wire mesh tubular structure or any other similar structure.

A preferred catalyst structure for the present hydrogenation reaction comprises flexible, semi-rigid open mesh tubular material, such as stainless steel wire mesh, filled with a particulate catalytic material in one of several embodiments recently developed in conjunction with the hydrogenation process.

One new catalyst structure developed for use in hydrogenations is described in U.S. Pat. No. 5,266,546 which is incorporated herein in its entirety. Briefly the new catalyst structure is a catalytic distillation structure comprising flexible, semi-rigid open mesh tubular material, such as stainless steel wire mesh, filled with a particulate catalytic material said tubular material having two ends and having a length in the range of from about one-half to twice the diameter of said tubular material, a first end being sealed together along a first axis to form a first seam and a second end being sealed together along a second axis to form a second seam wherein the plane of the first seam along the axis of said tubular material and the plane of the second seam along the axis of said tubular material bisect each other at an angle of about 15 to 90°.

U.S. Pat. No. 4,242,530 and U.S. Pat. No. 4,443,559, which are incorporated herein, disclose supported catalyst in a plurality of pockets in a cloth belt or wire mesh tubular structures which is supported in the distillation column reactor by open mesh knitted stainless steel wire by twisting the two together into a helix.

U.S. Pat. No. 5,348,710, which is incorporated herein, describes several other suitable structures in the prior art and discloses new structures suitable for this process.

The particulate catalyst material may be a powder, small irregular chunks or fragments, small beads and the like. The particular form of the catalytic material in the structure is not critical, so long as sufficient surface area is provided to allow a reasonable reaction rate. The sizing of catalyst particles can be best determined for each catalytic material (since the porosity or available internal surface area will vary for different material and of course affect the activity of the catalytic material).

For the present hydrogenations the preferred catalyst structures for the packing are those employing the more open structure of permeable plates or screen wire.

Referring now to the FIG. 1 there is shown a simplified flow diagram in schematic of a one column embodiment. The crude cumene/AMS from a cumene oxidation process and containing cumene, AMS, acetone, benzene, ethylbenzene and low and high boiling carbonyls, is fed to the distillation column reactor 10 via flow line 101, preferably above the bed 12 of hydrogenation catalyst in the form of a catalytic distillation structure as described above. Hydrogen is fed below the bed via flow line 102. The side chains of AMS are hydrogenated in the bed while acetone, and low boiling carbonyls along with benzene, ethylbenzene and excess hydrogen, are distilled as overheads via flow line 103.

The bottoms 106 contain butyl benzene and heavies. The hydrogenated AMS and feed cumene are recovered via flow line 105 and may be recycled to the oxidation process.

In FIG. 2 there is shown a simplified flow diagram in schematic of a two column embodiment. The first column 20 is a topping column as described above. The crude cumene/AMS from a cumene oxidation process and containing cumene, AMS, acetone, benzene, ethylbenzene and low and high boiling carbonyls, is fed to the distillation column 20 via flow line 201. Acetone, low boiling carbonyls, benzene, and ethylbenzene are distilled as overheads via flow line 203. The bottoms containing butyl benzene and heavies are recovered in line 206. Purified cumene/AMS is recovered as a side draw via line 205 and is fed to the distillation column reactor 30, preferably into the reaction distillation zone comprising beds 32 and 33 of hydrogenation catalyst in the form of catalytic distillation structures as described above. Hydrogen is fed below the beds via flow line 202. The side chains of AMS are selectively hydrogenated in the bed. Cumene along with excess hydrogen, is distilled as overheads via flow line 208 to knockout drum 40 from which hydrogen is withdrawn via line 209 and cumene recovered via line 210. The recovered cumene may be recycled to the oxidation process.

The bottoms purge is recovered via flow line 207 and may be recycled to the topping column 20.

Such conventional items as reboilers, overhead condensers and reflux streams have been omitted as being known within the art.

EXAMPLE

The feed to the process was a purified AMS concentrate from a phenol plant. It consisted of 18 wt % AMS, 81.2 wt % cumene, and small amounts of acetone, mesityl oxide, ethyl benzene, styrene, isopropylcyclohexane and several unidentified components.

The feed was run in a 1"×25' catalytic distillation column with 20' of catalyst height in the lower portion of the column. The uppermost 5' section was filled with ¼" saddles. The 20' catalyst section was loaded with 0.98 lb of T2487 Pd-based catalyst from UCI. The feed to the column was introduced 10.5' from the bottom.

The operating pressure of the column was maintained at 15 psig, and this gave an average catalyst zone temperature of 345° F.

The feed was introduced at a rate of 2 lb/h, with 1.9 lb/h being removed overhead and 0.1 lb/h out the bottom. Hydrogen was fed into the reboiler of the column. Two different hydrogen rates were tested. The composition of the OH and bottom product are shown below at different hydrogen rates.

|  | OH Composition | Bottom Composition | Overall AMS Conversion |
| --- | --- | --- | --- |
| 50% excess $H_2$ | 5.7 wt % AMS | 61 wt % AMS | 53% |
| 100% excess $H_2$ | 3.8 wt % AMS | 63 wt % AMS | 63% |

The invention claimed is:

1. A process for the selective hydrogenation of the side chains of α-methyl styrene impurities in a cumene stream comprising the steps of:

(a) feeding a stream containing cumene, α-methyl styrene, acetone, benzene, ethyl benzene, high boiling carbonyls and low boiling carbonyls to a distillation column wherein a first overheads comprising acetone and low boiling carbonyls is removed; butyl benzene and high boiling carbonyls are taken as a first bottoms stream and a stream containing cumene and α-methyl styrene is removed as a side draw:

(b) feeding said side draw stream and hydrogen to a distillation column reactor having a distillation reaction zone containing a hydrogenation catalyst;

(c) concurrently in said distillation column reactor
  (i) contacting the side draw stream with the hydrogen in said distillation reaction zone to hydrogenate a portion of the side chains of said α-methyl styrene without hydrogenating aromatic unsaturation to form a reaction mixture comprising components of said side draw stream, hydrogen and products of the reaction, and
  (ii) separating cumene from the reaction mixture by fractional distillation,
  (iii) while operating said distillation column reactor at less than 50 psig;

(d) withdrawing a stream comprising cumene and having a lower concentration of α-methyl styrene than said feed stream from said distillation column reactor as a second overheads;

(e) withdrawing heavier material from said distillation column reactor as a second bottoms; and (f) recycling said second bottoms to said distillation column.

2. The process according to claim 1 wherein said hydrogenation catalyst is a component of a distillation structure.

3. The process according to claim 2 wherein the hydrogen is present in a molar excess to the α-methyl styrene.

4. The process according to claim 2 wherein said side draw is fed into the distillation reaction zone and hydrogen is fed below the distillation reaction zone.

5. The process according to claim 4 wherein the hydrogenation catalyst comprises a noble metal on a support.

6. A process for the selective hydrogenation of the side chain of α-methyl styrene impurities in a cumene stream comprising the steps of:

(a) feeding a stream containing cumene, α-methyl styrene, acetone, benzene, ethyl benzene, high boiling carbonyls and low boiling carbonyls to a distillation column reactor;

(b) feeding hydrogen to said distillation column reactor;

(c) concurrently in said distillation column reactor
  (i) contacting the stream with hydrogen in said distillation reaction zone with a hydrogenation catalyst to hydrogenate a portion of the side chains of said α-methyl styrene without hydrogenating aromatic unsaturation to form a reaction mixture comprising components of said stream, hydrogen and products of the reaction at a pressure of between 160 and 250° C., and
  (ii) separating cumene from the reaction mixture by fractional distillation,
  (iii) while operating said distillation column reactor at less than 50 psig;

(d) withdrawing a stream comprising acetone and low boiling carbonyls from said distillation column reactor as an overheads stream;

(e) withdrawing heavier material comprising butyl benzene and high boiling carbonyls from said distillation column reactor as a bottoms stream; and (f) withdrawing a side draw stream comprising cumene and having a lower concentration of α-methyl styrene than said feed stream.

7. The process according to claim 6 wherein the pressure is in the range of atmospheric to about 45 psig.

8. The process according to claim 6 wherein said hydrogenation catalyst is a component of a distillation structure.

9. The process according to claim 8 wherein the hydrogen fed is greater than the α-methyl styrene concentration on a molecular basis.

10. The process according to claim 9 wherein the hydrogen fed is 1/1 to 10/1 moles for each mole of α-methyl styrene in the feed.

11. The process according to claim 10 wherein the hydrogenation catalyst comprises a noble metal on a support.

* * * * *